(12) United States Patent
Jackson

(10) Patent No.: US 8,377,100 B2
(45) Date of Patent: Feb. 19, 2013

(54) CLOSURE FOR OPEN-HEADED MEDICAL IMPLANT

(76) Inventor: Roger P. Jackson, Prairie Village, KS (US)

( * ) Notice: Subject to any disclaimer, the term of this patent is extended or adjusted under 35 U.S.C. 154(b) by 2416 days.

(21) Appl. No.: 10/142,614

(22) Filed: May 9, 2002

(65) Prior Publication Data

US 2002/0133159 A1 Sep. 19, 2002

Related U.S. Application Data

(63) Continuation-in-part of application No. 10/014,434, filed on Nov. 9, 2001, now Pat. No. 6,726,687, which is a continuation-in-part of application No. 09/732,528, filed on Dec. 7, 2000, now Pat. No. 6,454,772.

(51) Int. Cl.
  *A61B 17/70* (2006.01)
  *F31B 31/00* (2006.01)

(52) U.S. Cl. .............. 606/264; 606/270; 411/5

(58) Field of Classification Search ............ 606/73, 606/61, 54–57, 264, 270; 411/2–5, 405, 411/407; 81/176.15; 52/584.1; 184/105.3
See application file for complete search history.

(56) References Cited

U.S. PATENT DOCUMENTS

| | | | |
|---|---|---|---|
| 1,300,275 A * | 4/1919 | Johnson ............. | 411/407 |
| 1,330,673 A | 2/1920 | Anderson | |
| 2,083,092 A | 1/1936 | Richer | |
| 2,201,087 A | 5/1940 | Hallowell | |
| 2,239,352 A | 4/1941 | Cherry | |
| 2,295,314 A | 9/1942 | Whitney | |
| 2,537,029 A | 8/1946 | Cambern | |
| 2,445,978 A | 7/1948 | Stellin | |
| 2,532,815 A | 12/1950 | Kindsvatter | |
| 2,553,337 A | 5/1951 | Shafer | |
| 2,778,265 A | 1/1957 | Brown | |
| 2,969,250 A | 1/1959 | Kull | |
| 2,877,681 A | 3/1959 | Brown | |
| 2,927,332 A | 3/1960 | Moore | |
| 3,143,029 A | 8/1964 | Brown | |
| D200,217 S | 2/1965 | Curtiss | |
| 3,370,341 A | 2/1968 | Allsop | |
| 3,498,174 A | 3/1970 | Schuster et al. | |
| 3,584,667 A | 6/1971 | Reiland | |
| 3,640,416 A | 2/1972 | Temple | |
| 3,812,757 A | 5/1974 | Reiland | |
| 3,963,322 A | 6/1976 | Cryctko | |
| 4,103,422 A | 8/1978 | Weiss | |

(Continued)

FOREIGN PATENT DOCUMENTS

| | | |
|---|---|---|
| DE | 3630863 | 3/1988 |
| DE | 373809 | 5/1989 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Julian Woo
(74) *Attorney, Agent, or Firm* — John C. McMahon

(57) ABSTRACT

A closure for an open headed medical implant, such as a bone screw. The closure having a cylindrical body having an axis of rotation and also having a radially outer surface with a thread or other guide and advancement structure thereon. The body having a plurality of apertures that open onto a top surface of the body and that are parallel to but spaced from the axis of rotation. The closure also has a break-off head centrally attached by a neck to the top surface of the body.

18 Claims, 2 Drawing Sheets

U.S. PATENT DOCUMENTS

| | | | |
|---|---|---|---|
| 4,227,429 A * | 10/1980 | Bowers et al. | 81/176.15 |
| 4,269,246 A | 5/1981 | Larson et al. | |
| 4,373,754 A | 2/1983 | Bollfrass et al. | |
| 4,492,500 A | 1/1985 | Ewing | |
| 4,506,917 A | 3/1985 | Hansen Arne | |
| 4,577,448 A * | 3/1986 | Howorth | 52/584.1 |
| 4,600,224 A | 7/1986 | Blose | |
| 4,641,636 A | 2/1987 | Cotrel | |
| 4,703,954 A | 11/1987 | Ortloff et al. | |
| 4,707,001 A | 11/1987 | Johnson | |
| 4,763,644 A | 8/1988 | Webb | |
| 4,764,068 A | 8/1988 | Crispell | |
| 4,790,297 A | 12/1988 | Luque | |
| 4,805,602 A | 2/1989 | Puno et al. | |
| 4,815,453 A | 3/1989 | Cotrel | |
| 4,838,264 A | 6/1989 | Bremer et al. | |
| 4,850,775 A | 7/1989 | Lee | |
| 4,946,458 A | 8/1990 | Harms et al. | |
| 5,005,562 A | 4/1991 | Cotrel | |
| 5,022,791 A | 6/1991 | Isler | |
| 5,026,373 A | 6/1991 | Ray et al. | |
| 5,067,955 A | 11/1991 | Cotrel | |
| 5,073,074 A | 12/1991 | Corrigan et al. | |
| 5,092,635 A | 3/1992 | DeLange et al. | |
| 5,129,388 A | 7/1992 | Vignaud et al. | |
| 5,147,360 A | 9/1992 | Dubousset | |
| 5,154,719 A | 10/1992 | Cotrel | |
| 5,176,483 A | 1/1993 | Baumann et al. | |
| 5,207,678 A | 5/1993 | Harms et al. | |
| 5,217,497 A | 6/1993 | Mehdian | |
| 5,261,907 A | 11/1993 | Vignaud et al. | |
| 5,261,912 A | 11/1993 | Frigg | |
| 5,275,601 A | 1/1994 | Gogolewski et al. | |
| 5,282,707 A | 2/1994 | Palm | |
| 5,312,404 A | 5/1994 | Asher et al. | |
| 5,321,901 A | 6/1994 | Kelly | |
| 5,334,203 A * | 8/1994 | Wagner | 606/61 |
| 5,346,493 A | 9/1994 | Stahurski et al. | |
| 5,354,299 A | 10/1994 | Coleman | |
| 5,358,289 A | 10/1994 | Banker et al. | |
| 5,360,431 A | 11/1994 | Puno et al. | |
| 5,364,400 A | 11/1994 | Rego, Jr. et al. | |
| 5,382,248 A | 1/1995 | Jacobson et al. | |
| 5,385,583 A | 1/1995 | Cotrel | |
| 5,387,212 A | 2/1995 | Yuan et al. | |
| 5,395,371 A | 3/1995 | Miller et al. | |
| 5,427,418 A | 6/1995 | Watts | |
| 5,429,639 A | 7/1995 | Judet | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,487,742 A | 1/1996 | Cotrel | |
| 5,496,321 A | 3/1996 | Puno et al. | |
| 5,499,892 A | 3/1996 | Reed | |
| 5,507,747 A | 4/1996 | Yuan et al. | |
| 5,545,165 A | 8/1996 | Biedermann et al. | |
| 5,554,157 A | 9/1996 | Errico et al. | |
| 5,562,663 A | 10/1996 | Wisnewski et al. | |
| 5,569,247 A | 10/1996 | Morrison | |
| 5,584,834 A | 12/1996 | Errico et al. | |
| 5,586,984 A | 12/1996 | Errico et al. | |
| 5,591,166 A | 1/1997 | Bernhardt et al. | |
| 5,591,235 A | 1/1997 | Kuslich | |
| 5,601,553 A | 2/1997 | Trebing et al. | |
| 5,607,304 A | 3/1997 | Bailey et al. | |
| 5,607,426 A | 3/1997 | Ralph et al. | |
| 5,624,442 A | 4/1997 | Mellinger et al. | |
| 5,630,817 A | 5/1997 | Rokegem et al. | |
| 5,641,256 A | 6/1997 | Gundy | |
| 5,643,260 A | 7/1997 | Doherty | |
| 5,643,261 A | 7/1997 | Schafer et al. | |
| 5,647,873 A | 7/1997 | Errico et al. | |
| 5,653,710 A | 8/1997 | Harle | |
| 5,662,652 A | 9/1997 | Schafer et al. | |
| 5,669,911 A | 9/1997 | Errico et al. | |
| 5,672,176 A | 9/1997 | Biedermann et al. | |
| 5,681,319 A | 10/1997 | Biedermann et al. | |
| 5,683,390 A | 11/1997 | Metz-Stavenhagen et al. | |
| 5,690,630 A | 11/1997 | Errico et al. | |
| 5,697,929 A | 12/1997 | Mellinger | |
| 5,713,705 A * | 2/1998 | Grunbichler | 411/5 |
| 5,713,898 A | 2/1998 | Stucker et al. | |
| 5,716,356 A | 2/1998 | Biedermann et al. | |
| 5,725,527 A | 3/1998 | Biedermann et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,741,254 A | 4/1998 | Henry et al. | |
| 5,782,833 A | 7/1998 | Haider | |
| 5,797,911 A * | 8/1998 | Sherman et al. | 606/61 |
| 5,800,435 A | 9/1998 | Errico et al. | |
| 5,800,547 A | 9/1998 | Schafer et al. | |
| 5,817,094 A | 10/1998 | Errico et al. | |
| 5,863,293 A | 1/1999 | Richelsoph | |
| D407,302 S | 3/1999 | Lawson | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,303 A | 5/1999 | Eckhof et al. | |
| 5,944,465 A | 8/1999 | Janitzki | |
| 5,954,725 A | 9/1999 | Sherman et al. | |
| 5,961,517 A | 10/1999 | Biedermann et al. | |
| 5,964,760 A | 10/1999 | Richelsoph | |
| 6,001,098 A | 12/1999 | Metz-Stavenhagen et al. | |
| 6,004,349 A | 12/1999 | Jackson | |
| 6,010,503 A | 1/2000 | Richelsoph et al. | |
| 6,019,759 A | 2/2000 | Rogozinski | |
| 6,022,350 A | 2/2000 | Ganem | |
| 6,053,078 A | 4/2000 | Parker | |
| 6,053,917 A | 4/2000 | Sherman et al. | |
| 6,056,753 A | 5/2000 | Jackson | |
| 6,059,786 A | 5/2000 | Jackson | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,102,913 A | 8/2000 | Jackson | |
| 6,110,172 A | 8/2000 | Jackson | |
| 6,113,601 A | 9/2000 | Tatar | |
| 6,117,137 A | 9/2000 | Halm et al. | |
| 6,132,431 A | 10/2000 | Nilsson et al. | |
| 6,132,432 A | 10/2000 | Richelsoph | |
| 6,132,434 A | 10/2000 | Sherman et al. | |
| 6,139,550 A | 10/2000 | Michelson | |
| 6,143,032 A | 11/2000 | Schafer et al. | |
| 6,146,383 A | 11/2000 | Studer et al. | |
| 6,149,533 A | 11/2000 | Finn | |
| 6,183,472 B1 | 2/2001 | Lutz | |
| 6,187,005 B1 | 2/2001 | Brace et al. | |
| 6,193,719 B1 | 2/2001 | Gournay et al. | |
| RE37,161 E | 5/2001 | Michelson et al. | |
| 6,224,596 B1 | 5/2001 | Jackson | |
| 6,224,598 B1 | 5/2001 | Jackson | |
| 6,235,034 B1 | 5/2001 | Bray | |
| 6,248,105 B1 | 6/2001 | Schlapfer et al. | |
| 6,254,146 B1 | 7/2001 | Church | |
| 6,254,602 B1 | 7/2001 | Justis | |
| 6,261,039 B1 | 7/2001 | Reed | |
| 6,273,888 B1 | 8/2001 | Justis | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,296,642 B1 * | 10/2001 | Morrison et al. | 606/61 |
| 6,302,888 B1 | 10/2001 | Mellinger | |
| 6,309,391 B1 | 10/2001 | Crandall et al. | |
| 6,315,564 B1 | 11/2001 | Levisman | |
| 6,322,108 B1 * | 11/2001 | Riesselmann et al. | 411/2 |

| | | | | | | |
|---|---|---|---|---|---|---|
| 6,331,179 B1 | 12/2001 | Freid et al. | | 6,770,075 B2 | 8/2004 | Howland |
| 6,349,794 B2 * | 2/2002 | Spencer ................... 184/105.3 | | 6,780,186 B2 | 8/2004 | Errico et al. |
| 6,355,040 B1 | 3/2002 | Richelsoph et al. | | 6,790,209 B2 | 9/2004 | Beale et al. |
| RE37,665 E | 4/2002 | Ralph et al. | | 6,827,719 B2 | 12/2004 | Ralph et al. |
| 6,368,321 B1 | 4/2002 | Jackson | | 6,830,571 B2 | 12/2004 | Lenke et al. |
| 6,402,752 B2 | 6/2002 | Schaffler-Wachter et al. | | 6,835,196 B2 | 12/2004 | Biedermann et al. |
| 6,440,135 B1 | 8/2002 | Orgay et al. | | 6,840,940 B2 | 1/2005 | Ralph et al. |
| 6,440,137 B1 | 8/2002 | Horvath et al. | | 6,843,791 B2 | 1/2005 | Serhan |
| 6,443,953 B1 | 9/2002 | Perra et al. | | 6,858,031 B2 | 2/2005 | Morrison et al. |
| 6,451,021 B1 | 9/2002 | Ralph et al. | | 6,869,432 B2 | 3/2005 | Schlapfer et al. |
| 6,454,772 B1 | 9/2002 | Jackson | | 6,869,433 B2 | 3/2005 | Glascott |
| 6,471,703 B1 | 10/2002 | Ashman | | 6,872,208 B1 | 3/2005 | McBride et al. |
| 6,471,705 B1 | 10/2002 | Biedermann et al. | | 791,548 A1 | 6/2005 | Fischer |
| 6,485,492 B1 | 11/2002 | Halm et al. | | 6,932,817 B2 | 8/2005 | Baynham et al. |
| 6,485,494 B1 | 11/2002 | Haider | | 6,945,972 B2 | 9/2005 | Frigg et al. |
| 6,488,681 B2 | 12/2002 | Martin et al. | | 6,953,462 B2 | 10/2005 | Liebermann |
| 6,508,818 B2 | 1/2003 | Steiner et al. | | 6,955,677 B2 | 10/2005 | Dahners |
| 6,520,962 B1 | 2/2003 | Taylor et al. | | 6,958,065 B2 | 10/2005 | Ueyama et al. |
| 6,520,963 B1 | 2/2003 | McKinley | | 6,964,664 B2 | 11/2005 | Freid et al. |
| 6,527,804 B1 | 3/2003 | Gauchet et al. | | 6,964,665 B2 | 11/2005 | Thomas et al. |
| 6,530,929 B1 | 3/2003 | Jusis et al. | | 6,974,460 B2 | 12/2005 | Carbone et al. |
| 6,533,786 B1 | 3/2003 | Needham et al. | | 6,979,334 B2 | 12/2005 | Dalton |
| 6,540,749 B2 | 4/2003 | Schafer et al. | | 6,981,973 B2 | 1/2006 | McKinley |
| 6,547,790 B2 | 4/2003 | Harkey, III et al. | | RE39,035 E | 3/2006 | Finn et al. |
| 6,551,320 B2 | 4/2003 | Liebermann | | 7,018,378 B2 | 3/2006 | Biedermann et al. |
| 6,551,323 B2 | 4/2003 | Doubler et al. | | 7,018,379 B2 | 3/2006 | Drewry et al. |
| 6,554,832 B2 | 4/2003 | Shluzas | | 7,306,606 B2 | 12/2007 | Sasing |
| 6,554,834 B1 | 4/2003 | Crozet et al. | | 2001/0001119 A1 | 5/2001 | Lombardo |
| 6,558,387 B2 | 5/2003 | Errico et al. | | 2002/0026193 A1 | 2/2002 | Barker et al. |
| 6,562,040 B1 | 5/2003 | Wagner | | 2002/0035366 A1 | 3/2002 | Walder et al. |
| 6,565,565 B1 | 5/2003 | Yuan et al. | | 2002/0045898 A1 | 4/2002 | Freid et al. |
| 6,565,567 B1 | 5/2003 | Haider | | 2002/0072751 A1 | 6/2002 | Jackson |
| 6,582,436 B2 | 6/2003 | Schlapfer et al. | | 2002/0082602 A1 | 6/2002 | Biedermann et al. |
| 6,582,466 B1 | 6/2003 | Gauchet | | 2002/0111626 A1 | 8/2002 | Ralph et al. |
| 6,585,740 B2 | 7/2003 | Schlapfer et al. | | 2002/0133154 A1 | 9/2002 | Saint Martin |
| 6,595,992 B1 | 7/2003 | Wagner et al. | | 2002/0143341 A1 | 10/2002 | Biedermann et al. |
| 6,595,993 B2 | 7/2003 | Donno et al. | | 2002/0173789 A1 | 11/2002 | Howland |
| 6,602,255 B1 | 8/2003 | Campbell et al. | | 2002/0193795 A1 | 12/2002 | Gertzbein et al. |
| 6,610,063 B2 | 8/2003 | Kumar et al. | | 2003/0023243 A1 | 1/2003 | Biedermann et al. |
| 6,613,050 B1 | 9/2003 | Wagner et al. | | 2003/0028191 A1 | 2/2003 | Shluzas |
| 6,623,485 B2 | 9/2003 | Doubler et al. | | 2003/0073996 A1 | 4/2003 | Doubler et al. |
| 6,626,907 B2 | 9/2003 | Campbell et al. | | 2003/0093078 A1 | 5/2003 | Ritland |
| 6,626,908 B2 | 9/2003 | Cooper et al. | | 2003/0100896 A1 | 5/2003 | Biedermann et al. |
| 6,635,059 B2 | 10/2003 | Randall et al. | | 2003/0105460 A1 | 6/2003 | Crandall et al. |
| 6,648,885 B1 | 11/2003 | Friesem | | 2003/0125741 A1 | 7/2003 | Biedermann et al. |
| 6,648,887 B2 | 11/2003 | Ashman | | 2003/0149432 A1 | 8/2003 | Frigg et al. |
| 6,656,179 B1 | 12/2003 | Schaefer et al. | | 2003/0163133 A1 | 8/2003 | Altarac et al. |
| 6,656,181 B2 | 12/2003 | Dixon et al. | | 2003/0176862 A1 | 9/2003 | Taylor et al. |
| 6,660,004 B2 | 12/2003 | Barker et al. | | 2003/0199873 A1 | 10/2003 | Richelsoph |
| 6,663,632 B1 | 12/2003 | Frigg | | 2003/0208204 A1 | 11/2003 | Bailey et al. |
| 6,663,635 B2 | 12/2003 | Frigg et al. | | 2003/0216735 A1 | 11/2003 | Altarac et al. |
| 6,673,073 B1 | 1/2004 | Schafer | | 2004/0006342 A1 | 1/2004 | Altarac et al. |
| 6,676,661 B1 | 1/2004 | Benlloch et al. | | 2004/0092934 A1 | 5/2004 | Howland |
| 6,679,833 B2 | 1/2004 | Smith et al. | | 2004/0097933 A1 | 5/2004 | Lourdel et al. |
| 6,682,529 B2 | 1/2004 | Stahurski | | 2004/0116929 A1 | 6/2004 | Barker et al. |
| 6,689,133 B2 | 2/2004 | Morrison et al. | | 2004/0138662 A1 | 7/2004 | Landry et al. |
| 6,689,134 B2 | 2/2004 | Ralph et al. | | 2004/0143265 A1 | 7/2004 | Landry et al. |
| 6,695,843 B2 | 2/2004 | Biedermann et al. | | 2004/0147929 A1 | 7/2004 | Biedermann et al. |
| 6,695,851 B2 | 2/2004 | Zdeblick et al. | | 2004/0158247 A1 | 8/2004 | Sitiso et al. |
| 6,699,249 B2 | 3/2004 | Schlapfer et al. | | 2004/0162560 A1 | 8/2004 | Raynor et al. |
| 6,706,045 B2 | 3/2004 | Lin et al. | | 2004/0172022 A1 | 9/2004 | Landry et al. |
| 6,712,818 B1 | 3/2004 | Michelson | | 2004/0172032 A1 | 9/2004 | Jackson |
| 6,716,213 B2 | 4/2004 | Shitoto | | 2004/0176766 A1 | 9/2004 | Shluzas |
| 6,716,214 B1 | 4/2004 | Jackson | | 2004/0186473 A1 | 9/2004 | Cournoyer et al. |
| 6,716,247 B2 | 4/2004 | Michelson | | 2004/0193160 A1 | 9/2004 | Richelsoph |
| 6,723,100 B2 | 4/2004 | Biedermann et al. | | 2004/0210216 A1 | 10/2004 | Farris et al. |
| 6,726,689 B2 | 4/2004 | Jackson | | 2004/0225289 A1 | 11/2004 | Biedermann et al. |
| 6,730,093 B2 | 5/2004 | Saint Martin | | 2004/0236330 A1 | 11/2004 | Purcell et al. |
| 6,730,127 B2 | 5/2004 | Michelson | | 2004/0249380 A1 | 12/2004 | Glascott |
| 6,733,502 B2 | 5/2004 | Altarac et al. | | 2004/0267264 A1 | 12/2004 | Konieczynski et al. |
| 6,736,816 B2 | 5/2004 | Ritland | | 2005/0027296 A1 | 2/2005 | Thramann et al. |
| 6,736,820 B2 | 5/2004 | Biedermann et al. | | 2005/0049589 A1 | 3/2005 | Jackson |
| 6,740,086 B2 | 5/2004 | Richelsoph | | 2005/0055026 A1 | 3/2005 | Biedermann et al. |
| 6,746,449 B2 | 6/2004 | Jones et al. | | 2005/0070899 A1 | 3/2005 | Doubler et al. |
| 6,755,829 B1 | 6/2004 | Bono et al. | | 2005/0080415 A1 | 4/2005 | Keyer et al. |
| 6,755,835 B2 | 6/2004 | Schultheiss et al. | | 2005/0096653 A1 | 5/2005 | Doubler |
| 6,755,836 B1 | 6/2004 | Lewis | | 2005/0107788 A1 | 5/2005 | Beaurain et al. |
| 6,761,723 B2 | 7/2004 | Buttermann et al. | | 2005/0113927 A1 | 5/2005 | Malek |
| 6,767,351 B2 | 7/2004 | Orbay et al. | | 2005/0131404 A1 | 6/2005 | Mazda et al. |

| | | | | | |
|---|---|---|---|---|---|
| 2005/0131413 A1 | 6/2005 | O'Driscoll et al. | EP | 1121902 | 8/2001 |
| 2005/0149023 A1 | 7/2005 | Ritland | EP | 1190678 | 3/2002 |
| 2005/0154389 A1 | 7/2005 | Selover et al. | EP | 1210914 | 6/2002 |
| 2005/0154391 A1 | 7/2005 | Doherty et al. | EP | 1277444 | 1/2003 |
| 2005/0159750 A1 | 7/2005 | Doherty | EP | 1449486 | 8/2004 |
| 2005/0165400 A1 | 7/2005 | Fernandez | EP | 1570795 | 9/2005 |
| 2005/0171540 A1 | 8/2005 | Lim et al. | EP | 1579816 | 9/2005 |
| 2005/0187548 A1 | 8/2005 | Butler et al. | EP | 1634537 | 3/2006 |
| 2005/0187555 A1 | 8/2005 | Biedermann et al. | FR | 2467312 | 4/1981 |
| 2005/0192580 A1 | 9/2005 | Dalton | FR | 2729291 | 7/1996 |
| 2005/0203511 A1 | 9/2005 | Wilson-MacDonald et al. | FR | 2796545 | 1/2001 |
| 2005/0203516 A1 | 9/2005 | Biedermann et al. | FR | 2856578 | 6/2003 |
| 2005/0216003 A1 | 9/2005 | Biedermann et al. | FR | 2865373 | 1/2004 |
| 2005/0228501 A1 | 10/2005 | Miller et al. | FR | 2865375 | 1/2004 |
| 2005/0234450 A1 | 10/2005 | Barker | FR | 2865377 | 1/2004 |
| 2005/0234451 A1 | 10/2005 | Markworth | FR | 2857850 | 4/2004 |
| 2005/0234452 A1 | 10/2005 | Malandain | FR | 2865378 | 10/2004 |
| 2005/0240181 A1 | 10/2005 | Boomer et al. | GB | 203508 | 9/1923 |
| 2005/0240183 A1 | 10/2005 | Vaughan | GB | 2082709 | 3/1982 |
| 2005/0251137 A1 | 11/2005 | Ball | GB | 2140523 | * 11/1984 |
| 2005/0251141 A1 | 11/2005 | Frigg et al. | GB | 2365345 | 2/2002 |
| 2005/0261687 A1 | 11/2005 | Garamszegi et al. | JP | 9-504727 | 5/1997 |
| 2005/0267474 A1 | 12/2005 | Dalton | RU | 371359 | 2/1993 |
| 2005/0273099 A1 | 12/2005 | Baccelli et al. | WO | 92/03100 | 3/1992 |
| 2005/0273101 A1 | 12/2005 | Schumacher | WO | WO92/03101 | 3/1992 |
| 2005/0277919 A1 | 12/2005 | Slivka et al. | WO | 94/10927 | 5/1994 |
| 2005/0277925 A1 | 12/2005 | Mujwid | WO | 94/10944 | 5/1994 |
| 2005/0277928 A1 | 12/2005 | Boschert | WO | WO94/10927 | 5/1994 |
| 2005/0283152 A1 | 12/2005 | Lindemann et al. | WO | WO94/10944 | 5/1994 |
| 2005/0283157 A1 | 12/2005 | Coates et al. | WO | WO94/26191 | 11/1994 |
| 2005/0283238 A1 | 12/2005 | Reiley | WO | WO95/35067 | 12/1995 |
| 2005/0288669 A1 | 12/2005 | Abdou | WO | 96/06576 | 3/1996 |
| 2005/0288671 A1 | 12/2005 | Yuan et al. | WO | WO96/06576 | 3/1996 |
| 2005/0288673 A1 | 12/2005 | Catbagan et al. | WO | WO96/28118 | 9/1996 |
| 2006/0004357 A1 | 1/2006 | Lee et al. | WO | WO97/14366 | 4/1997 |
| 2006/0004359 A1 | 1/2006 | Kramer et al. | WO | WO98/32386 | 7/1998 |
| 2006/0004360 A1 | 1/2006 | Kramer et al. | WO | WO01/49191 | 7/2001 |
| 2006/0004363 A1 | 1/2006 | Brockmeyer et al. | WO | WO02/054966 | 7/2002 |
| 2006/0009769 A1 | 1/2006 | Lieberman | WO | WO03/068088 | 8/2003 |
| 2006/0009770 A1 | 1/2006 | Speirs et al. | WO | WO2004/021900 | 3/2004 |
| 2006/0015104 A1 | 1/2006 | Dalton | WO | WO2004/041100 | 5/2004 |
| 2006/0025767 A1 | 2/2006 | Khalili | WO | WO2004/089245 | 10/2004 |
| 2006/0025768 A1 | 2/2006 | Iott et al. | WO | WO2004/107997 | 12/2004 |
| 2006/0025770 A1 | 2/2006 | Schlapfer et al. | WO | WO2005/000136 | 1/2005 |
| 2006/0036242 A1 | 2/2006 | Nilsson et al. | WO | WO2005/000137 | 1/2005 |
| 2006/0036252 A1 | 2/2006 | Baynham et al. | WO | WO2005/020829 | 3/2005 |
| 2006/0052783 A1 | 3/2006 | Dant et al. | WO | WO2005/072632 | 8/2005 |
| 2006/0052784 A1 | 3/2006 | Dant et al. | WO | WO2005/082262 | 9/2005 |
| 2006/0052786 A1 | 3/2006 | Dant et al. | WO | WO2005/099400 | 10/2005 |
| 2006/0058788 A1 | 3/2006 | Hammer et al. | WO | WO2006/012088 | 2/2006 |
| | | | WO | WO2006/017616 | 2/2006 |
| | FOREIGN PATENT DOCUMENTS | | WO | WO2006/028537 | 3/2006 |
| DE | 9202745.8 | 3/1992 | | | |
| DE | 4425392 | 11/1995 | | | |
| DE | 19507141 | 9/1996 | | | |
| DE | 19509331 | 9/1996 | | | |
| DE | 28910798 | 12/1999 | | | |
| DE | 29810798 | 12/1999 | | | |
| DE | 19951145 | 5/2001 | | | |
| DE | 10157969 | 2/2003 | | | |
| EP | 195455 | 9/1986 | | | |
| EP | 172130 | 2/1987 | | | |
| EP | 0276153 | 7/1988 | | | |
| EP | 276153 | 7/1988 | | | |
| EP | 465158 | 1/1993 | | | |
| EP | 0885598 | 12/1998 | | | |
| EP | 1090595 | 4/2001 | | | |

OTHER PUBLICATIONS

EBI Omega 21 Brochure, EBI Spine Systems, pub. 1999.
SDRS Surgical Dynamics Rod System Brochure, Surgical Dynamics, pub. 1998-99.
Spine, Lipcott, Williams & Wilkins, Inc. vol. 24, No. 15, p. 1495.
The Rod Plate System Brochure, Stryker Howmedica Osteonics, pub. Oct. 1999.
Versalok Low Back Fixation System Brochure, Wright Medical Technology, Inc., pub. 1997.
VLS System Variable Locking Screw Brochure, Interpore Cross International, 1999.

* cited by examiner

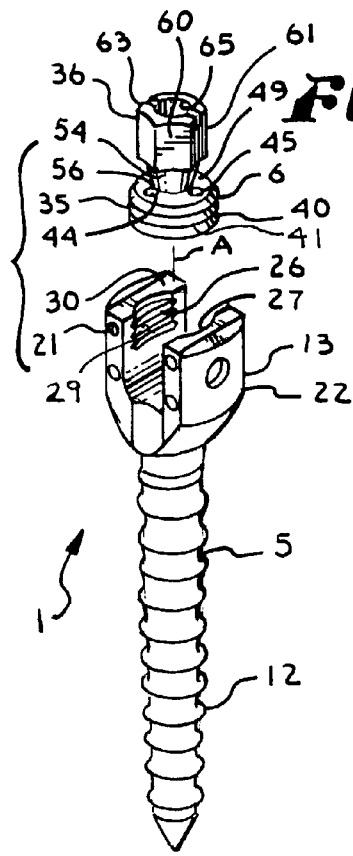
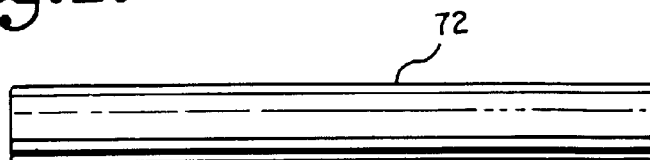
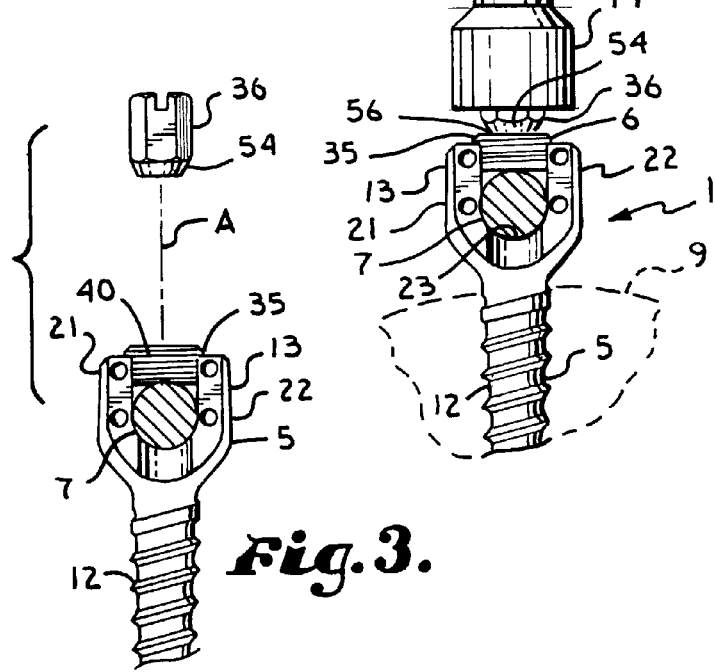

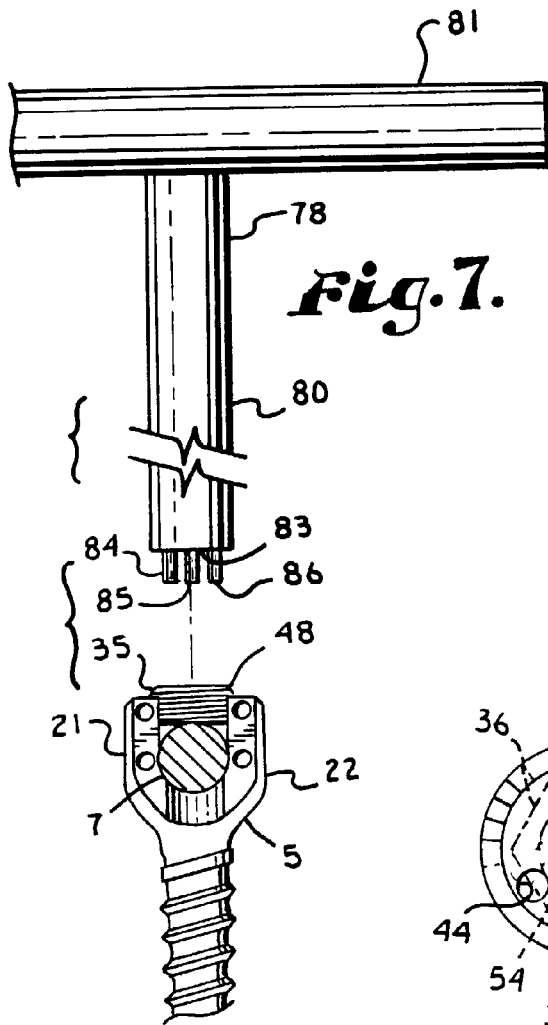
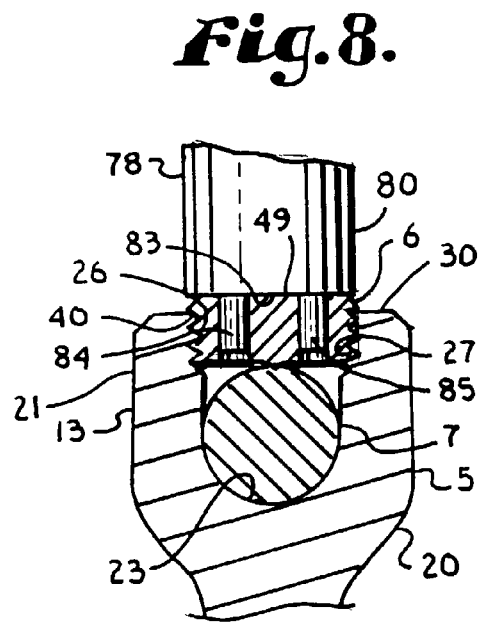
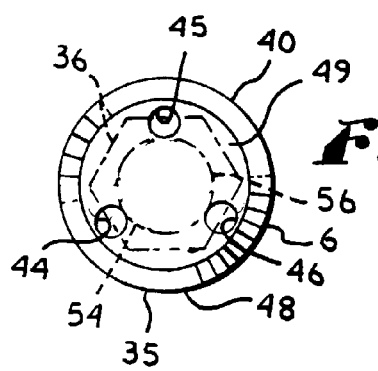
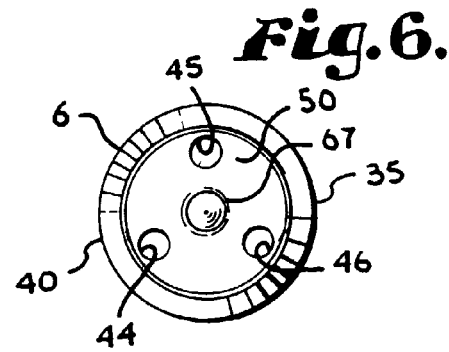

CLOSURE FOR OPEN-HEADED MEDICAL IMPLANT

CROSS REFERENCE TO RELATED APPLICATIONS

The present application is a continuation-in-part of U.S. Ser. No. 10/014,434 filed Nov. 9, 2001, now U.S. Pat. No. 6,726,687 which was a continuation-in-part of U.S. Ser. No. 09/732,528, filed Dec. 7, 2000, now U.S. Pat. No. 6,454,772.

BACKGROUND OF THE INVENTION

The present invention is directed to an open headed medical implant and, in particular, to a closure for closing the head of an open headed bone screw, hook or the like.

Bone screws are used especially in spinal surgery to support and position various implants needed to repair a spine that has suffered injury, illness or genetic defect. Bone screws of this type are screwed into the vertebrae of the spine and have a head that projects outside the bone which receives other implants, such as rods, that extend along the spine. Bone screws are of two general types which are either open headed or closed headed. Hooks and certain other implants also sometimes have open heads. The present application is directed to open headed bone screws and related implants such as hooks and the like that have such an open head to receive another implant.

In open headed bone screws and related implants, the head includes two upright arms that form a channel therebetween. The channel is sized to receive a rod or the like and is open to make it easier to place the rod in the head. The rod must then be tightly held or locked in the head to prevent relative movement between implants after the surgery. To hold the rod in the head, plugs have been used that are screwed into threads on the interior surfaces of the arms.

The present invention is directed especially to improvements in such plugs or closures that make them easier to insert in the head, that better ensure that the plug effectively secures the rod so that the rod does not later slip, that allow the plugs to be easily removed should the overall implant system require rearrangement and which provide a comparatively low profile, so as reduce trauma and irritation to the surrounding tissues of the patient.

SUMMARY OF THE INVENTION

A closure is provided for an open headed implant, especially a bone screw or hook for use in spinal surgery. The closure has a cylindrical shaped body with an axis of rotation. The body has a radially outer surface that has a thread or other guide and advancement structure thereon that is sized and shaped to be received in mating threads or structure on interior surfaces of arms of the implant head. The closure is operably rotated and advanced into the head of the implant to capture a rod or other part of an overall spinal support system. The closure captures and locks such a rod in position relative to the implant to prevent rotation or axial movement between the joined parts.

The closure body has a top surface and a bottom surface with a plurality of cylindrical bores extending parallel to the axis of rotation into the body from the top surface or other removal apertures. The bores or apertures are positioned in spaced relationship to one another and to the axis of rotation. The bores or apertures are sized and shaped to cooperatively mate with posts on a tool to allow removal of the closure from the implant after insertion, should such be necessary.

The closure also includes a break-off head centrally mounted by a neck on the top surface of the body. The break-off head is adapted to receive a socket tool and be rotated thereby during installation. The break-off head is also designed to break from the body at a torque limiting or break-off region or location which is preferably whereat the neck intersects with the top surface of the body, when a preselected torque is applied to the break-off head. When the break-off head is broken away, the bores or apertures become exposed and are mateable with a removal tool should it become necessary to remove the closure.

OBJECTS AND ADVANTAGES OF THE INVENTION

Therefore, the objects of the present invention are: to provide a closure for an open ended implant that provides a plurality of spaced removal apertures that are offset from an axis of rotation of the closure and that cooperate with a tool to allow removal of the closure; to provide such an implant having a closure with a break off head for mating with an insertion tool for inserting the closure into the implant; to provide such an implant wherein the removal apertures are not accessible for effective access, when the closure is in the implant until the break-off head is broken away; to provide such an implant that strongly grips a rod or the like received in the implant and that provides a relatively low profile; and to provide such an implant and closure therefor that is relatively easy to use, comparatively easy to produce and is especially well suited for the intended use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a bone screw type implant and closure in accordance with the present invention prior to insertion of the closure into a head of the bone screw.

FIG. 2 is a fragmentary side elevational view of the bone screw with a rod and the closure received therein and with a tool being utilized to insert the closure and provide torque to the break-off head of the closure and further with the bone screw shown embedded in a bone that is indicated by phantom lines.

FIG. 3 is a fragmentary and exploded side elevational view of the bone screw, rod and closure with the break-off head of the closure being shown broken therefrom.

FIG. 4 is a fragmentary top plan view of the bone screw, rod and closure with the break-off head removed.

FIG. 5 is a top plan view of the closure with the break-off head broken therefrom, but shown in phantom.

FIG. 6 is a bottom plan view of the closure.

FIG. 7 is an exploded and fragmentary side elevational view of the bone screw, rod and closure showing a removal tool positioned above the closure.

FIG. 8 is a fragmentary and enlarged view of the bone screw, rod and closure shown in FIG. 7 with the removal tool inserted into the closure and with portions of the bone screw and closure broken away to show detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a medical implant in accordance with the present invention. The implant 1 includes a bone screw 5, a closure 6 for the bone screw 5 and a rod 7. The implant 1 is received in a vertebrae 9, typically in conjunction with other implants that are not shown. The closure 6 also functions in conjunction with other open-headed implants, such as hooks and the like.

The bone screw 5 includes a shank 12 and a head 13. The shank 12 is threaded with a coarse helicably wound flighting-like thread 16 that is threaded into the vertebrae 9, so as to secure and support the bone screw 5 and allow the head 13 to extend from the vertebrae 9.

The bone screw head 13 includes a base 20 with a pair of upstanding spaced arms 21 and 22 on opposite sides of the base 20 forming a generally U-shaped configuration, when viewed from the side, and defining a channel 23 therebetween. The channel 23 is sized and shaped to receive the rod 7.

The arms 21 and 22 each include an interior surface 26 and 27 respectively. The interior surfaces 26 and 27 have a guide and advancement structure which in the illustrated embodiment is a partial helical wound thread 29 on each. While the illustrated thread 29 is a conventional V-shaped thread, the purpose of this thread is to engage similar threads on the closure 6 to guide the closure 6 relative to the bone screw 5, as discussed below, and to provide for biased advancement of the closure 6 along the central axis A thereof relative to the bone screw 5 upon rotation of the closure 6. It is foreseen that other structures including other types of threads, such as buttress and reverse angle threads, and non threads, such as helical wound flanges or the like having interlocking surfaces, could be alternatively used for this purpose. Therefore, the illustrated internal partial or discontinuous threads on the bone screw arms 21 and 22 along with the mating thread on the closure 5 provide guide and advancement structure that operably positions and advances the closure 6 relative to the bone screw 5 during installation. The threaded surfaces 26 and 27 are spaced and not connected so as to present only a partial threadform which each face one another and cooperate with the closure 6, as is noted below. In the illustrated embodiment, the threaded surfaces 26 and 27 extend from a top 30 of the bone screw 5 only partially down the arms 21 and 22.

The closure 6 includes a body 35 and a torque limiting break-off head 36. The closure body 35 is generally cylindrical in shape and has a radially outward external surface 40 that extends 360° about an axis of rotation indicated by the reference letter "A". In the present embodiment, the surface 40 has a portion of the mating guide and advancement structure thereon which in the illustrated embodiment is a thread 41 that mates with the partial thread 29 on the bone screw 5 and biases the closure 6 forward due to interaction of the threads 29 and 41 upon clockwise rotation of the closure 6. As noted before, this function can be provided by alternative types of threads or other non threaded structures such as a helicably wound flange that slidably mates with a similar structure on the bone screw 5. In the illustrated embodiment the threaded surface 40 has a threadform located thereon that entirely encircles the outer surface 40 of the body 35 and extends entirely from top to bottom. The surface 40 is provided with a thread 41 that is sized, shaped and configured to threadably mate with the threaded surfaces 26 and 27 of the arms 21 and 22, so that the closure body 35 may be threaded into the bone screw head 13, as is shown in FIG. 2.

The closure body 35 also includes at least one removal aperture and in the illustrated embodiment such an aperture is provided by three bores 44, 45 and 46 that are aligned to be parallel with the axis of rotation. The bores 44, 45 and 46 are spaced both from the axis of rotation A and from a periphery 48 of a top 49 of the body. The bores 44, 45 and 46 extend from the body top 49 to a bottom surface 50 of the body 35 in the illustrated embodiment. Preferably the bores 44, 45 and 46 are equally spaced from one another and are approximately equally radially spaced outward from the axis of rotation A. In the illustrated embodiment, the bores 44, 45 and 46 are spaced at approximately 120° from one another. While three cylindrical bores are shown and function as the removal aperture in the illustrated embodiment, it is foreseen that various numbers of openings could be equivalently used and/or such apertures may be of various shapes, such as round, square or kidney bean in cross section, and may be pass through from top 49 to bottom surface 50 of the closure 6 or may just pass through the top 49 thereof and extend partially therethrough.

The break-off head 36 includes a neck 54 that joins with the body top 49 at a torque limiting region or break-off location 56. Preferably the break-off location 56 is generally coplanar with the body top 49, so the break-off location 56 is clean and low profile after such breakoff. The break-off location 56 is normally determined by the location whereat the neck 54 is smallest in cross-section or the location 56 can be triggered by an external groove and other devices known for this purpose. The neck 54 also converges somewhat from the remainder of the break-off head 36 to the break-off location 56.

The break-off head 36 includes a number of facets or panels 60 which are aligned to be parallel to the axis of rotation A and which are joined together to form a polyhedral shaped surface 61 typically associated with a structure to be received in a socket-type tool. The combined surface 61 of the facets 60 forms such a polyhedral shape. A top surface 63 of the break-off head 36 has axially located therein a non-threaded bore 65 for operably receiving a tool during implantation. The bottom surface 50 of the body 35 includes a conical shaped and axially aligned point 67 for engaging and preferably biting into the rod 7, so as to provide an improved grip on the rod to prevent rotation or axial movement thereof relative to the bone screw 5. It is foreseen that the bottom surface 50 may be flat or otherwise shaped and may include other structure to increase frictional engagement between the closure 6 and the rod 7, such as: knurling; a ring with a sharp lower edge, especially when used in conjunction with and surrounding the point 67; or the like.

A tool 70 is illustrated in FIG. 2 for cooperatively inserting the closure 6 into the bone screw head 13. The tool 70 has an elongate shank 71 with a handle 72 sized and shaped to allow a user to rotate the tool 70 clockwise about the axis of rotation A associated with the closure 6. The tool 70 also has a socket type head 74 opposite the handle 72 that is sized and shaped to snugly receive the outer surface 61 of the break off head 36 as is shown in FIG. 2.

During assembly, the rod 7, which is elongate and generally circular in cross-section, is placed within the bone screw channel 23 and the closure 6 is then threaded into the bone screw head 13. The tool 70 is used to rotate the closure 6 until it engages the rod 7 and urges the rod 7 to seat tightly and snugly on the bone screw head base 20 at the bottom of the channel 23. The point 67 engages and digs into the rod 7. As additional torque is applied to the tool 70, a preselected torque is eventually reached (for example 90 inch pounds) whereat the break-off head 36 breaks from the closure body 35 at the break-off location 56 and separates therefrom, such as is shown in FIG. 3.

FIGS. 3 and 4 illustrate the closure 6 operably positioned within the bone screw head 13. FIG. 5 illustrates the closure 6 with the break-off head 36 removed, but shown in phantom to illustrate the position of the break-off head 36 relative to the bores 44, 45 and 46.

In certain circumstances, it is necessary to remove the closure 6 to readjust the position of the rod 7 or to make some other change in the implant 1 configuration. As mentioned before, the implant 1 is typically a part of an overall system and is normally used to provide support to damaged, injured or missing vertebra of the spinal column. When it is necessary to readjust the overall system, the closure 6 is removed by utilization of the second tool 78. The tool 78 includes a shank 80 that has an axis of rotation during use that is coaxial with the axis of rotation A of the closure 6. The shank 80 is attached at one end to a handle 81 to provide a grasp and a means of turning the tool 78 by a user. Opposite the handle 81, the shank 80 has a flat surface 83 from which three pegs or posts 84, 85 and 86 project.

The posts 84, 85 and 86 are parallel to the axis of rotation of the tool 78 and are sized, shaped and positioned so as to be snugly receivable in the closure bores 44, 45 and 46, subsequent to removal of the break-off head 36. The tool 78 is shown in position above the closure body 35 in FIG. 7 just prior to insertion of the posts 84, 85 and 86 into respective bores 44, 45 and 46. The tool 78 is shown positioned with the posts 84, 85 and 86 in the respective bores 44, 45 and 46 in FIG. 8. The purpose of the tool 70 is to allow a user to rotate the closure body 35 counter-clockwise and remove the body 35 from the bone screw head 13 after the closure 6 has been seated therein. In this way the channel 23 can be reopened and the rod 7 removed or repositioned relative to the bone screw head 13.

While the non-axially located bores 44, 45 and 46 of the present embodiment are located between the break-off head neck 54 and the periphery 48, it is foreseen that one or more non-axial bores of this type could partially or entirely intersect with the neck 54 so as to become fully open or exposed at the closure top surface 49 only when a break-off head associated with such a neck breaks from the closure body.

It is to be understood that while certain forms of the present invention have been illustrated and described herein, it is not to be limited to the specific forms or arrangement of parts described and shown.

What is claimed and desired to be secured by Letters Patent is as follows:

1. A closure plug in combination with an open-headed medical implant having a pair of spaced arms with a discontinuous, helically wound interior guide and advancement structure thereon; said plug comprising:
  a) a body sized and shaped to be received between the arms of the implant; said body having a radially outward surface that has a mating guide and advancement structure thereon that is sized and shaped to rotatably mate with the interior guide and advancement structure of the arms of the implant;
  b) said body having a top surface and a bottom surface; said top surface of said body having at least one removal aperture therein sized and shaped to receive a removal tool; said aperture extending axially from the bottom surface to the top surface of said body and opening onto the top surface thereof;
  c) said aperture being spaced from and positioned between both a central axis of said body and a periphery of said body; and
  d) a break-off head breakably and axially joined to said body and adapted to receive an installation tool for operably rotating said body; said head being joined to said body by a torque limiting region that causes said head to break from the body, when a preselected torque is applied to said head; said break-off head being free of pass through openings that axially align with said apertures so as to operably block axial access to said aperture from above said break-off head by the removal tool until said break-off head breaks from said body.

2. The combination according to claim 1 wherein:
  a) there are a pair of spaced apertures extending into said body from the top surface thereof.

3. The combination according to claim 1 wherein:
  a) said body is generally cylindrical in shape.

4. The combination according to claim 1 including:
  a) said break-off head is joined to said body by a neck; said neck being aligned with the central axis of said body.

5. The combination according to claim 4 wherein:
  a) said body includes at least a pair of said apertures in the top thereof; and
  b) said neck is positioned between said apertures.

6. The combination according to claim 4 wherein:
  a) said break-off head has a tool grippable outer surface for operably rotating said closure during insertion into an implant and said neck being sized and shaped to include said torque limiting region, such that said break-off head breaks from said body when said preselected torque is applied to said break-off head by such a gripping tool with a generally clean profile at said top surface.

7. The combination according to claim 1 wherein:
  a) said interior guide and advancement structure and said mating guide and advancement structure are respective mating discontinuous helical wound threads on bone screw arms of the implant and mating helical wound threads on said closure plug body.

8. The combination according to claim 1 wherein:
  a) said aperture is a cylindrical bore and said body top surface has three such bores sized and shaped to be adapted to receive the removal tool located therein; each of said bores being located at a common radius from said body central axis and being spaced at 120° from adjacent tool receiving bores.

9. The combination according to claim 1 including:
  a) a tool having a grippable handle and an engagement face; said face including a post extending parallel to an axis of rotation of said tool for each said body aperture; each said posts being sized, aligned and positioned to simultaneously enter a respective aperture so as to rotate and apply torque to said body when said tool is rotated about the axis thereof, whereby said tool is operable to at least remove said body from an implant in which said body has been inserted.

10. An open headed medical implant having:
  a) a first element adapted to operably be joined to a bone or other implant;
  b) an implant head secured to said first element and having a pair of upright spaced arms defining a channel therebetween; said arms each having facing and discontinuous interior surfaces with helically wound interior guide and advancement structure on each arm;

c) a closure for closing said channel between said arms; said closure comprising:
   i) a body sized and shaped to be received between the arms of said head; said body having a radially outward surface that has a mating guide and advancement structure thereon that is sized and shaped to rotatably mate with the interior guide and advancement structure of the arms of said head;
   ii) said body having a top and a bottom; said body having at least one axially extending aperture therein with said aperture opening onto said body top and being sized and shaped to receive a removal tool;
   iii) said aperture being spaced from and positioned between both a central axis of said body and a periphery of said body;
   iv) a break-off head breakably and axially joined to said body and adapted to receive an installation tool for operably rotating said body; said break-off head being joined to said body by a torque limiting region that causes said break-off head to break from said body, when a preselected torque is applied to said break-off head; said break-off head being free of openings that are axially aligned with said aperture to prevent axial passage through said break-off head into said aperture by the removal tool so as to operably prevent axial access by the removal tool to said aperture from above said break-off head until after said break-off head breaks from said body.

11. The implant according to claim 10 wherein:
a) there are a pair of spaced aperture extending into said body from the top surface thereof.

12. The implant according to claim 10 wherein:
a) said body is generally cylindrical in shape.

13. The implant according to claim 12 wherein:
a) said body includes at least a pair of said apertures in the top thereof; and
b) neck is positioned between said apertures.

14. The implant according to claim 10 including:
a) said break-off head is joined to said body by a neck; said neck being aligned with the central axis of said body.

15. The implant according to claim 14 wherein:
a) said break-off head has a tool grippable outer surface for operably rotating said closure during insertion into said implant head and said neck being sized and shaped to include said torque limiting region, such that said break-off head breaks from said body when said preselected torque is applied to said break-off head by such a gripping tool with a generally clean profile at said top surface.

16. The implant according to claim 10 wherein:
a) said aperture is a cylindrical bore and said body top surface has three such bores sized and shaped to be adapted to receive the removal tool located therein; each of said bores being located at a common radius from said body central axis and being spaced at 120° from adjacent tool receiving bores.

17. The implant according to claim 10 including:
a) a tool having a grippable handle and an engagement face; said face including a post extending parallel to an axis of rotation of said tool for each said body aperture; each of said posts being sized, aligned and positioned to simultaneously enter a respective aperture so as to rotate and apply torque to said body when said tool is rotated about the axis thereof, whereby said tool is operable to at least remove said body from said implant head in which said body has been inserted.

18. An open headed medical implant having:
a) a first element adapted to operably be joined to a bone or other implant;
b) an implant head secured to said first element and having a pair of upright spaced arms defining a channel therebetween; said arms each having facing interior surfaces with interior guide and advancement structure thereon;
c) a closure for closing said channel between said arms; said closure comprising:
   i) a body sized and shaped to be received between the arms of said head; said body having a radially outward surface that has a mating guide and advancement structure thereon that is sized and shaped to rotatably mate with the interior guide and advancement structure of the arms of said head;
   ii) said body having a top and a bottom; said top of said body having at least one axially aligned aperture therein opening onto the top thereof and being sized and shaped to receive a removal tool;
   iii) said aperture being spaced from and positioned between both a central axis of said body and a periphery of said body;
   iv) a break-off head breakably axially joined to said body and adapted to receive an installation tool for operably rotating said body; said break-off head being joined to said body by a torque limiting region that causes said break-off head to break from said body, when a preselected torque is applied to said break-off head; said break-off head being free of pass through openings that align with said aperture so as to operably block axial access to said aperture by said removal tool until said break-off head breaks from said body; and
d) said interior guide and advancement structure and said mating guide and advancement structure are discontinuous helical wound threads on the implant head and helical wound mating threads on said closure body.

* * * * *